United States Patent [19]

Epstein

[11] Patent Number: 4,761,499

[45] Date of Patent: Aug. 2, 1988

[54] CARBONYLATION OF VINYL DIHALIDES

[75] Inventor: Ronald A. Epstein, Yonkers, N.Y.

[73] Assignee: Akzo America Inc., New York, N.Y.

[21] Appl. No.: 56,636

[22] Filed: Jun. 2, 1987

Related U.S. Application Data

[63] Continuation-in-part of Ser. No. 945,257, Dec. 22, 1986, which is a continuation-in-part of Ser. No. 796,687, Nov. 12, 1985, Pat. No. 4,668,816.

[51] Int. Cl.$^4$ .................... C07C 51/14; C07C 102/00; C07C 67/36
[52] U.S. Cl. .................... 562/520; 564/132; 560/97; 560/207
[58] Field of Search ............. 560/97, 207; 562/520; 564/132

[56] References Cited

U.S. PATENT DOCUMENTS 2,565,462  8/1951  Prichard et al. .................... 562/520
3,991,101  11/1976  Knifton .............................. 562/520

OTHER PUBLICATIONS

Chemical Abstract 14087 (9–C) vol. 64, 1966.

*Primary Examiner*—Paul J. Killos
*Attorney, Agent, or Firm*—Richard P. Fennelly; Francis W. Young; Louis A. Morris

[57] ABSTRACT

High yields of olefinic esters and amides, and the like are derived from a process wherein vinyl dihalides are carbonylated in the presence of a palladium catalyst and a primary or secondary amine base or tertiary amine, depending on the desired product, and a solvent.

18 Claims, No Drawings

CARBONYLATION OF VINYL DIHALIDES

CROSS-REFERENCE TO RELATED APPLICATIONS

This is a continuation-in-part of co-pending application Ser. No. 945,257, filed Dec. 22, 1986, which is a continuation-in-part of application Ser. No. 796,687, filed Nov. 12, 1985, now U.S. Pat. No. 4,668,816.

BACKGROUND OF THE INVENTION

1. Field of the Invention

The invention is directed to the carbonylation of vinyl dihalides to produce novel amide compounds, olefinic esters, and the like.

2. Related Art

It is known to carbonylate halo-hydrocarbons such as benzyl chloride by reaction with carbon monoxmide and an alcohol at 100° C. or below and at atmospheric pressure in the presence of an amine and a catalytic amount of a palladium catalyst to form esters.

An article entitled "Palladium-Catalyzed Carboalkoxylation of Aryle, Benzyl, and Vinylic Halides" by A. Schoenberg et al. appearing in The Journal of Organic Chemistry, Vol. 39, page 3318 (1974) discloses a process whereby aryl and vinylic bromides and iodides and benzyl chloride are each reacted with carbon monoxide and an alcohol at 100° C. or below and at atmospheric pressures in the presence of a tertiary amine and a catalytic amount of a palladium-triphenylphosphine complex to form esters. The article does not disclose processes utilizing vinyl dihalides, nor the preparation of novel amines or esters of vinyl dihalide.

U.S. Pat. No. 3,116,306 discloses a process for preparing carboxylated organic compounds by reacting (1) an organic compound represented by the general formula $R_nZ$ in which R is an organic compound having at least one aliphatic radical or cycloaliphatic radical, Z is $SO_4$, X, $X_2$ or $R'SO_3$, X being a halogen and R' is alkyl, alkenyl, cycloalkyl, aryl or aralkyl, where n is 1, Z is X, $X_2$ or $R'SO_3$, and when n is 2, Z is $SO_4$, the Z substituent being attached to an aliphatic or cycloaliphatic primary or secondary carbon atom; (2) carbon monoxide; (3) a salt of a metal hydrocarbonyl of the group consisting of cobalt hydrotetracarbonyl and iron dihydrotetracarbonyl and (4) a material of the group consisting of water, alcohols, phenols, mercaptans, ammonia, hydrazine, primary organo-nitrogen bases and secondary organo-nitrogen bases. This patent discloses that tertiary amines such as dicyclohexylethylamine have been found to be of general use in the process of the invention.

U.S. Pat. No. 4,480,121 describes the reaction of a hydrocarbon stream with a hydrogen halide to produce 2halo-1-alkenes. The invention further comprised preparing acrylate esters by contacting the 2-halo-1-alkene with carbon monoxide and an esterifying agent.

In a paper entitled "Carboxymethylation of Organic Halides by Palladium Complexes under Mild Conditions" by Masanobu Hidai et al. appearing in the Bulletin of the Chemical Society of Japan, Vol. 48 (7), pages 2075–2077 (1975) there is disclosed the attempted carboxymethylation of various organic dihalides to their corresponding esters under what are described as very mild conditions. The article discloses that the carbonylation of organic dihalides was unsuccessful since they did not afford corresponding esters. The amine used in the process and those disclosed were secondary amines.

In none of the above references is there taught, suggested or shown the carbonylation of organic dihalides to produce corresponding amides or esters using secondary or tertiary amines.

U.S. Pat. No. 4,128,554 discloses the preparation of carboxylic acid amides from organic halides. The process disclosed is the reaction of an aryl, heterocyclic, or vinylic halide and substituted derivates thereof with a primary or secondary amine and carbon monoxide in the presence of a palladium catalyst and, if necessary, a tertiary amine at temperatures of about 20°–150° C. and at least a half atmosphere of pressure. There is no disclosure relevant to using vinyl dihalides in the process disclosed.

A paper entitled, "Synthesis of Diynes, Alpha, BetaUnsaturated Monoacids, and Diacids by the Selective Palladium (O)-Catalyzed and Phase Transfer Catalyzed Reactions of Vinylic Dibromids" by Galamb et al. appearing in Organometallics, 1983, pp. 801–805, teaches the alpha and beta-unsaturated monoacids and diacids were the products formed by reacting vinylic dibromides with carbon monoxide using a zero valent palladium catalyst.

SUMMARY OF THE INVENTION

A novel process whereby olefinic esters, amides, and the like can be obtained, and wherein novel amide compounds are prepared under mild conditions by the carbonylation of vinyl dihalides has been discovered. The process for producing the amides comprises carbonylating the vinyl dihalides in the presence of an inert solvent, a soluble palladium catalyst, and an amine. The amine can comprise a primary or secondary amine, however, a tertiary amine can also be present. The reaction is conducted in the presence of a tertiary amine to produce the esters of the invention. For producing esters, the solvent is an alcohol and the amine is a tertiary amine.

DETAILED DESCRIPTION OF THE INVENTION

The process comprises the carbonylation of vinyl dihalides in the presence of a solvent under relatively mild conditions to give amides and esters, using a soluble palladium catalyst combined with a phosphine ligand in the presence of an amine base. The invention comprises the use of a primary, secondary, or tertiary amine base, depending upon the desired product, in conjunction with a soluble palladium catalyst.

Vinyl dihalides suitable for the purposes of this invention are 1,1- and 1,2-dihaloethylene, propylene, 1-butene, and the like.

Any primary, secondary or tertiary amine can be used in the practice of the invention. Suitable amines for practicing the invention to form amides are, for example, methyl, ethyl, propyl and butyl amine, and dimethyl, diethyl, dipropyl and dibutyl amines, and the like. Suitable tertiary amines include trimethyl, triethyl, tributyl and diisopropylethyl, dicylocohexylethyl amines, and the like.

The novel amide compounds produced by the process disclosed include (N,N,N', N' tetraethyl)-2-methylene propanamide and 3-(N',N' diethlamine) N,N diethyl propenamide having the formulas $CH_2=C(CON(C_2H_5)_2)_2$ and $(C_2H_5)_2N—CH=CH-CON(C_2H_5)_2$.

In preparing the esters by the process disclosed, a tertiary amine is used in the process, since the presence of a primary or secondary amine would also produce amides. Amides are prepared using primary and secondary amines. It should be evident that the preparation of esters in the practice of the invention comprises reacting the vinyl dihalide with carbon monoxide in the presence of an alcohol which serves not only as the solvent for the system, but as an active ingredient in the reaction.

In preparing the novel amides, the solvent utilized should be non-reactive and solubilize the reaction components. Therefore, a suitable solvent for this process comprises aromatic and substituted aromatic solvents such as benzene, toluene, and xylene.

Catalysts for practicing the invention are derived from palladium (II) complexes exemplified by the general formula $PdX_2L_2$ where X=halide and L=tertiary phosphine or a group such as benzonitrile which will exchange with tertiary phosphine in solution or $PdX_4{}^{2-}$ or $PdCl_2$ which will react with tertiary phosphine to yield $PdX_2L_2$; or palladium (O) complexes exemplified by (1) $PdL_n$ where L=tertiary phosphine and n=2–4, or L=dibenzylidene acetone and n=2 (which will react with tertiary phosphine in solution), (2) $Pd_x(CO)_yL_z$ where L=tertiary phosphine, x=y=1 and z=3 or x=y=3, z=3 or 4. These complexes may be prepared in situ or prior to being added to the reaction.

It has been found that suitable catalysts include $PdCl_2(PPh_3)_2$, $PdCl_2(PhC\equiv N)_2$, and $PdCl_2(CH_3C\equiv N)_2$. The moiety ($PPh_3$) is triphenyl phosphine.

The amount of catalyst utilized in the process ranges from about 10 mole % of the halo-hydrocarbon to about 0.01 mole % and preferably from about 0.6 to about 0.02 mole %.

An excess of carbon monoxide over theoretical stoichiometric requirements is utilized in the process. Preferably a large excess of carbon monoxide is employed and the reaction is usually and conveniently carried out in an atmosphere of carbon monoxide. However, pure carbnon monoxide need not necessarily be used in this reaction and mixtures of carbon monoxide with such gases as nitrogen, argon, methane, ethane, and the like, which are inert with respect to the carbonylation reaction, are entirely satisfactory for the purposes of this invention.

A wide range of pressure has been found suitable for the purposes of this invention, from about atmospheric or less to about 351.54 Kg/sq.cm (5,000 lbs/in$^2$) or more. Pressures of from about atmospheric to about 35,15 Kg/sq.cm (500 lbs/in$^2$) are desirable, while from atmospheric to 100 lbs/in$^2$ (7.03 Kg/cm$^2$) are preferred. Similarly, the process of this invention can be carried out within a wide range of temperatures, from about 0° C. to about 150° C. or even higher. Preferred temperatures are from about 40° C. to about 100° C. The formation of some products is more rapid as compared to other products. As such, the preferred process temperature necessary for preparing the various products may vary considerably.

Typical alcohols suitable for the purposes of this invention include aliphatic alcohols such as methyl alcohol, ethyl alcohol, propyl alcohol, isopropyl alcohol, n-butyl alcohol, secondary butyl alcohol, n-hexyl alcohol, hexanol-2, n-octyl alcohol, capryl alcohol, isopropyl dodecyl alcohol, and the like; polyhydric compounds such as ethylene glycol, diethylene glycol, glycerol, pentaerythritol, and the like; olefinic alcohols such as allyl alcohol, crotyl alcohol, buten-1-ol-4, pent-en-1-ol-5, and the like; cycloaliphatic alcohols, such as cyclopentyl alcohol, cyclohexyl alcohol, methyl cyclohexyl alcohol, and the like; aralkyl alcohols such as benzyl alcohol, phenylethyl alcohol, phenyl propyl alcohol, cinnamyl alcohol, and the like.

Although practicing the invention under anhydrous conditions is also desirable, the instant invention may also be practiced in the presence of water.

It will be apparent from the foregoing description, therefore, that the present invention provides new useful products and a process for preparing such products. Furthermore, the carboxylated organic compounds produced thereby are suitable for various conventional uses for such products, such as monomers or plasticizers for polymeric materials, as surface active agents, and the like.

The following Examples are descriptive of the process of the invention.

EXAMPLE 1

Into a 12-oz. heavy wall glass reactor equipped with a gas inlet and outlet, thermocouple, and magnetic stir bar was placed 53.0 mg $PdCl_2(PPh_3)_2$ (0.076 mmole) and 19.6 mg $PPh_3$ (0.075 mmole). The reactor was evacuated and filled with $N_2$. Under a $N_2$ purge, deoxygenated 1,1 dichloroethylene, 1.55 g (16 mmole), diethyl amine, 4.62 g (63 mmole), and 17.3 g toluene were added.

The reactor was flushed with CO, pressurized to 30 psig and heated to 100° C. The reactor was then maintained at 45 psig by feeding CO to the reactor on demand. After 6 hours at 100° C., the reactor was cooled and vented.

Gas Chromatography (GC) and GC/Mass Spectometry (MS) analysis identified the products of the dichloroethylene carbonylation as the novel amide derivatives $CH_2=C(CONEt_2)_2$, $Et_2NCH=CHCONEt_2$, and a trace of the $CH_2=CCl(CONEt_2)$.

EXAMPLE 2

The reactor described in Example 1 was equipped with a mechanical stirrer and a liquids inlet line. Using the same procedure as in Example 1, the reactor was charged with 0.201 g $PdCl_2(PPh_3)_2$ (0.287 mmole), 0.224 g $PPh_3$ (0.855 mmole), 6.12 g $CH_2=CCl_2$ (63.1 mmole) and 68 g toluene. To a separate $N_2$ filled flask 3.13 g $HNEt_2$ (42.8 mmole), 6.20 g $EtN(i-Pr)_2$ (48.0 mmole) and 28 g of toluene was added. The reactor was pressurized with 30 psig CO and heated to 100° C.

By means of a metering pump, 34 ml of the amine solution was added to the solution in the reactor, at 100°, 45 psig CO over 4¾ hours. The reactor was maintained at 100°, 45 psig CO, for an additional 20 minutes, then cooled and vented. GC analysis showed the formation of the diamide $CH_2=C(CONEt_2)_2$ and the presence of a trace amount of $CH_2=CCl(CONEt_2)$.

EXAMPLE 3

The carbonylation of $CH_2=CCL_2$ was carried out as in Example 2, except that $Pd(PPh_3)_4$, 0.36 g (0.31 mmole), was added to the reactor instead of $PdCl_2(PPh_3)_2$ and $PPh_3$. $CH_2=C(CONEt_2)_2$ and a trace amount of $CH_2=CCl(CONEt_2)$ were identified by GC.

EXAMPLE 4

The reactor system of Example 1 equipped with a mechanical stirrer was charged with 0.33 g $Pd(PPh_3)_4$ (0.29 mmole), 6.45 g trans 1,2 dichloroethylene (66.5 mmole), 18.3 g HNEt$_2$(250 mmole), and 54 g toluene. The carbonylation was run as in Example 1 for 3 hours. Et$_2$NCH=CHCONEt$_2$ was identified as the major product of the carbonylation.

EXAMPLE 5

Following the procedure of Example 4, 6.33 g (68.4 mmole) trans CHCl=CHCl, 18.29 g (142 mmole) EtN(i-Pr)$_2$, and 50 g (0.83 mole) isopropanol were reacted at 100° C., 45 psig CO, for 3 hours and 40 minutes in the presence of 0.33 g (0.29 mmole) Pd(PPh$_3$)$_4$. Diisopropyl fumarate was identified as the product of the carbonylation.

What is claimed is:

1. A process for carbonylating a vinyl dihalide to esters or amides comprising carbonylating, a vinyl dihalide in the presence of a solvent for the process, using carbon monoxide and amine, and a palladium catalyst.
2. The process of claim 1 wherein the ester is prepared in the presence of an alcohol solvent and a tertiary amine.
3. The process of claim 1 wherein the amine is ethylamine.
4. The process of claim 1 wherein the amine is diethylamine.
5. The process of claim 2 wherein the tertiary amine is diisopropylethylamine.
6. The process of claim 1 wherein the palladium catalyst is palladium II complexes having the formula PdX$_2$L$_2$ wherein X is a halide and L is a tertiary phosphine.
7. The process of claim 6 wherein the palladium catalyst is PdCl$_2$(PPh$_3$)$_2$.
8. The process of claim 1 wherein the palladium catalyst is a palladium II complex having the formula PdX$_2$L$_2$, wherein X is a halide and L is benzonitrile.
9. The process of claim 1 wherein the vinyl dihalide is 1,1-dichloroethylene or 1,2-dichloroethylene.
10. The process of claim 8 wherein the benzonitrile reacts with phosphine in situ.
11. The process of claim 2 wherein the alcohol is isopropanol.
12. The process of claim 2 wherein the alcohol is methanol.
13. The process of claim 1 conducted under anhydrous conditions.
14. An amide compound having the formula CH$_2$=C(CON(C$_2$H$_5$)$_2$)$_2$.
15. An amide compound of the formula (C$_2$H$_5$)$_2$N—CH=CHCON(C$_2$H$_5$)$_2$.
16. The process of claim 1 wherein the amides are prepared in the presence of a primary or secondary amine and an inert solvent.
17. The process of claim 16 wherein the solvent used is an aromatic or substituted aromatic solvent.
18. The process of claim 17 wherein the solvent is toluene.

* * * * *